United States Patent [19]

Donohue et al.

[11] 3,992,435

[45] Nov. 16, 1976

[54] PROCESS FOR ELECTROLYTIC SYNTHESIS OF POLYALKYLBIPHENYLPOLYCARBOXYLIC ACID COMPOUNDS

[75] Inventors: John A. Donohue, Elmhurst; Ellis K. Fields, River Forest, both of Ill.; Harold Hart, Okemos, Mich.

[73] Assignee: Standard Oil Company, Chicago, Ill.

[22] Filed: Apr. 7, 1975

[21] Appl. No.: 565,356

[52] U.S. Cl. .......................... 260/475 R; 204/59 R; 260/515 P
[51] Int. Cl.² ...................... C25B 3/10; C07C 69/76
[58] Field of Search ........................... 204/59 R, 78; 260/475 R, 515 P

[56] References Cited
FOREIGN PATENTS OR APPLICATIONS
1,181,688    9/1961    Germany ............................... 204/59

*Primary Examiner*—R. L. Andrews
*Attorney, Agent, or Firm*—William C. Clarke; Arthur G. Gilkes; William T. McClain

[57] ABSTRACT

Process for coupling alkyl esters of polyalkylbenzoic acid to prepare polyalkylbiphenylpolycarboxylic acid compounds which comprises anodically oxidizing said alkyl esters in a non-nucleophilic media by applying a source of direct current in liquid phase at atmospheric pressure and temperatures from −30° to 80° C. The biphenyl acid compounds are useful in the formation of polyester resins, including alkyds, and fiber-forming polymers.

12 Claims, No Drawings

PROCESS FOR ELECTROLYTIC SYNTHESIS OF POLYALKYLBIPHENYLPOLYCARBOXYLIC ACID COMPOUNDS

BACKGROUND OF THE INVENTION

This invention relates to a process for the electrolytic anodic coupling of alkyl polyalkylbiphenyldicarboxylates and the polyalkylbiphenyldicarboxylic acids prepared thereby. Ortho polyalkylbiphenyldicarboxylic acids are desirable starting materials for polyester resins, including alkyds, and for plasticizers. Meta polyalkylbiphenyldicarboxylic acids are desirable starting materials for polyester resins including alkyds, polyamide resins and fiber-forming polymers with outstanding properties for certain applications. It is known that the substituted biphenyl grouping reduces flexibility and increases rigidity.

Alkylbiphenylpolycarboxylic acids can be obtained by standard procedures using the classical Ullmann coupling reaction followed by complete oxidation of all the alkyl groups but the selective oxidation of the ortho and meta groups has not been successful. Moreover, the Ullmann reaction requires a halogen in the position on the aromatic ring where the coupling is to take place. Electronegative groups, such as nitro and methoxycarbonyl, particularly in the ortho position, strongly activate an aryl halogen. But on the other hand, the reaction is greatly inhibited or prevented by the presence of substituents which provide an alternative path for reaction of the aryl halide, such as amino, hydroxy, and free carboxyl groups. Bulky groups in the ortho positions may impede the reaction by steric hindrance. At best, the Ullmann reaction is a two-step reaction in that it requires the positioning of a halogen at the point on the ring where coupling is to take place, and coupling can be impeded because of ring substituents.

The oxidative coupling of monosubstituted benzenes with palladium salts has been reported by R. Van Helden and G. Verbug (Recueil, 84, 1965, 1263–1273). However, with di- and trisubstituted benzenes, steric factors were found to play an important role. From ortho xylene, 3,4,3',4' and 2,3,3',4' tetramethylbiphenyl were obtained as the only products. Mesitylene could not be converted into the corresponding biphenyl as might be expected. Thus, oxidative coupling with palladium catalyst has been reported to be handicapped by steric factors or the product tends to be of the para isomers rather than the ortho or meta isomer.

The electrolytic coupling of polymethyl benzene (mesitylene) to its biphenyl derivatives has been reported by L. Eberson and K. Nyberg ("Anodic Oxidations", ACS Div. of Pet. Chem., Chicago, Vol. 15, No. 4, Sept. 1970, B7). These investigators found that biaryl coupling was generally the major reaction mode for anodic oxidation of 1,3,5-trimethyl benzene (mesitylene) in non-nucleophilic (non-electron donating) media with a suitable electrolyte. Another type of anodic oxidation process is the well-known Kolbe synthesis whereby the anodic oxidation of a carboxylate structure is followed by decarboxylation and coupling to yield a di-grouping of the hydrocarbon or alkyl moiety in the carboxylate structure. It is equally well known that aromatic carboxylic acids in which the carboxyl group is directly attached to a benzene ring fail to undergo the Kolbe reaction to any extent, as is reported by B. C. L. Weedon ("Anodic Syntheses With Carboxylic Acids" Quarterly Reviews Vol. 6, No. 4, 1952 p. 387–388). Benzoic acid on electrolysis in methanol yields benzene rather than undergoing a coupling reaction. The electrolysis of 4-t-butyl-2,6-dimethyl benzoic acid in methanol gives 3-methyl-4-t-butyldimethyl phthalate and 1,3-dimethyl-5-t-butylbenzene rather than undergoing coupling.

We have now found that methyl polymethyl benzoates can be made to couple with the ester groups in the ortho and meta positions. This process is capable of producing the desired ortho and meta methyl dicarboxylates of polymethyl substituted biphenyls in good yields. These biphenyls have been prepared and there is evidence of one terphenyl in a gas chromatograph peak.

BRIEF SUMMARY OF THE INVENTION

This invention relates to a process for the electrolytic anodic coupling of alkyl polyalkylbiphenyldicarboxylates, specifically dimethyl 4,4', 6,6'-tetramethylbiphenyl-2,2'-dicarboxylate and dimethyl 2,2', 4,4', 6,6'-hexamethylbiphenyl-3,3'-dicarboxylate and their diacids. The coupling process utilizes non-nucleophilic media in an electrolysis cell at atmospheric pressure and temperatures from −30° to 80°C.

DETAILED DESCRIPTION OF INVENTION

Alkyl polyalkylbiphenyldicarboxylates and polyalkylbiphenyldicarboxylic acids, with the acid groups in the ortho and meta positions are prepared in a convenient manner by electrolytically coupling alkyl esters of substituted benzoic acid. The coupling reaction surprisingly occurs despite the presence of the ester groups on the benzene ring. The process utilizes anodic oxidation in non-nucleophilic media with tetrapropylammonium tetrafluoroborate as the supporting electrolyte. The products are the alkyl polyalkylbiphenyldicarboxylates. Hydrolysis by a strong acid yields the diacids.

For purposes of this invention, the term "alkyl ester of substituted benzoic acid" is defined as an aromatic compound with a carboxylic acid ester attached to the benzene ring and at least two alkyl groups attached to the benzene ring in the 3,5 positions. The reactant can be defined also as an aromatic compound with three alkyl groups attached to the benzene ring in the 2,4,6 positions with respect to the carboxylic acid ester, also attached to the ring. Since the desired alkyl polyalkylbiphenyldicarboxylates are those with the coupling linkage either ortho or meta to the benzene ring carboxylic acid ester group, it is necessary that the ring carbon atom in the required ortho or meta position be substituted only with hydrogen prior to the coupling reaction.

While methyl groups are the preferred alkyl substituents on the benzene ring and are the preferred alkyl group of the carboxylate moiety, it is not required that the groups be exclusively methyl. The reactants can be also aromatic compounds with alkyl substituents in the 3,5 positions, or with alkyl substituents in the 2,4,6 positions, such substituents including, but not limited to methyl, ethyl, and tertiary butyl groups. The ester is not limited to being the methyl ester but can be the ester of any conveniently and commonly available aliphatic alcohol having one to four carbon atoms in the alkyl moiety. The alkyl substituents attached to the benzene ring can be any alkyl group of one to four carbon atoms.

The methyl polymethyl benzoates given in the examples are coupled in the process of the invention by electrolytic anodic coupling in the liquid phase in non-nucleophilic media in an electrolysis cell at atmospheric pressure and at temperatures from −30° to 80° C. A convenient temperature range is from 20° to 40° C. In general, the electrolytic anodic coupling is conducted in a relatively concentrated solution, within the range of 0.5 to 4.0 molar, of the substrate in a non-aqueous solution.

It is beneficial to minimize undesirable reactions at the anode by the proper selection of the electrolyte constituents. Since aromatic compounds in an electrolytic solution can be oxidized at the anode to give cation radicals or dications, these then can react with the nucleophiles present, the substrate itself, the solvent, or the anion of the supporting electrolyte to give substitution or addition products. The formation of the dimer, trimer, and higher homologues will occur in electrolytic solutions where the substrate is the strongest nucleophile present.

The required electrolytic reactions of this invention were carried out by applying a suitable source of direct current to two platinum electrodes immersed in the electrically conducting solution of the organic compounds. Other electrode materials are known in the art and could have been selected from the group consisting of platinum black, gold and carbon. Acids, bases or salts are necessarily added to the solution usually to provide electrical conductivity since most organic compounds are non-conductors. Selection of the conducting substance requires that its oxidation or reduction occur with more difficulty than that of the organic compound. Tetraalkylammonium tetrafluoroborates, either the tetrapropyl or tetrabutylammonium tetrafluoroborate, are well-known as useful electrolytes for anodic processes in nonaqueous solvents. Acetonitrile, propylene carbonate, methylene chloride, dimethyl sulfoxide are known to be solvents with sufficiently high dielectric constants to promote ionization of the electrolyte when used alone.

Good yields of the coupled product are possible if the oligomers are removed rapidly. At low conversion, between 5 and 15%, solvent extraction can be used. The solvent can be an aliphatic hydrocarbon of a lower boiling point than that of the product. A typical solvent is heptane. Alternatively, an ether extraction of the residue is used. In an ether extraction, the electrolytic anodic coupling solvent is evaporated off, ether is added to extract the product away from the electrolytic salt, the ether is in turn evaporated off, and then the unreacted starting materials are vacuum-distilled from the oligomer product, which is the diester. The diacid is obtained by hydrolyzing the diester by dissolving it in a strong acid, concentrated sulfuric acid, with the application of heat. The reaction product is precipitated by addition of water. Repeated washing with water, followed by chloroform washes and air drying, yields the purified dicarboxylic acid.

In most electrolytic preparations, a divided cell is used. The anode is separated from the cathode by means of a diaphragm, often porous alumina, in order to prevent the oxidized product from being reduced and vice versa. In this instance, a polyethylene screen was used to electrically insulate the cathode from the anode and not as a diaphragm. Anode current efficiencies are normally not high. The actual number of ampere hours used is normally substantially greater than the theoretical amount of current necessary (53.6 ampere hours per mole of product, assuming two electrons per molecule of reagent), and often can be two times greater then theoretical. Preferable current efficiencies are, of course, closest to theoretical.

The electrolytic anodic coupling process of my invention provides a new method to prepare polyalkylbiphenyldicarboxylic acids and their alkylated esters which are new compositions of matter. The process operates by coupling polysubstituted alkyl-esters of benzoic acid in a solvent solution in an electrolysis cell. The electrolytic reactions of this invention are carried out by applying a suitable source of direct current to two electrodes immersed in the electrically conducting solution of the organic compounds. Preferably the electrodes are of platinum but other electrode materials can be used, namely, platinum black, gold and carbon. The coupling occurs in the liquid phase in non-nucleophilic media at atmospheric pressure and at temperatures from −30° to 80° C. The media is a solvent solution of a supporting electrolyte, the solvent being selected as one with a sufficiently high dielectric constant to promote ionization of the supporting electrolyte. The concentration of the substrate, i.e., the ester to be coupled, is within the range of 0.5 to 4.0 molar, with respect to the solvent. A convenient range is 1.5 to 2.5 molar. The solvent and supporting electrolyte are selected so as to result in an electrolysis solution where the substrate is the strongest nucleophile present. Direct current applied was within a current density range of 0.008 to 0.016 amperes/sq. centimeter. An economic commercial application would necessarily require a higher current density.

Good yields of the coupled product can result if the oligomers are removed rapidly. At low conversion, between 5 and 15%, solvent extraction can be used.

The new compositions of matter of my invention are alkyl polyalkylbiphenyldicarboxylates and polyalkylbiphenyldicarboxylic acids wherein the alkyl moieties of the alkyl esters and alkyl groups attached to the benzene ring comprise aliphatic groups having one to four carbon atoms. Specifically, these new ester compounds are dimethyl 4,4', 6,6'-tetramethylbiphenyl-2,2'-dicarboxylate (DTMBD) and dimethyl 2,2', 4,4'. 6,6'-hexamethylbiphenyl-3,3'-dicarboxylate (DHMBD). The new acid compounds are 4,4', 6,6'-tetramethylbiphenyl-2,2'-dicarboxylic acid (TMBDC) and 2,2', 4,4', 6,6'-hexamethylbiphenyl-3,3'-dicarboxylic acid (HMBDC).

There is a demand for new diesters and diacids with the biphenyl grouping and the acyl groups in the ortho and meta positions. The biphenyl grouping reduces flexibility and increases rigidity. The ortho acyl groups make the compound suitable for polyester resins including alkyds, and plasticizers for polymers of vinyl chloride. The meta acyl groups make the compound suitable for polyester resins, including alkyds, polyamide resins and fiber-forming polymers.

In order to facilitate a clear understanding of the invention, i.e., the process for electrolytic anodic coupling of methyl polymethyl benzoates and the polymethylbiphenyl diacids and dimethyl carboxylates prepared thereby, the following specific embodiments are described in detail. It should be understood, however, that the detailed expositions of the process and the resulting new compositions of matter, while indicating preferred embodiments, are given by way of illustration only since various changes and modifications within the spirit and scope of the invention will become apparent to those skilled in the art from this detailed description.

EXAMPLE 3,5-Dimethylbenzoic acid, 99% pure, having a melting point of 168°–171°C, was esterified before electrolysis by refluxing in methanol containing 20% hydrochloric acid (HCl). 50.0 Grams of 3,5-dimethylbenzoic acid was dissolved in 500 ml of a standard solution of 20% (wgt.) of HCl in purified anhydrous methanol prepared by running gaseous HCl into the methanol to achieve the 20% (wgt.) level. The solution was heated at reflux for two hours, maintaining reflux conditions by means of a water-cooled condenser. Heat to the 1000 ml. round-bottom flask was supplied by an electric heating mantle. The reaction was stopped at the end of two hours.

The resulting ester was isolated by dissolving the reaction product in ether followed by extraction with water to remove the HCl and methanol. The ether solution was separated in a separatory funnel, dried over anhydrous calcium sulfate and filtered. The dried ether solution was distilled to remove the ether. The residue, which was the ester, was purified by vacuum distillation in a round-bottom flask. Pot temperature was 87° C at 2.5 mm Hg. Yield was 27.7 grams of ester. Re-working of the water washings yielded 21.0 grams of a heavy material from which more ester was obtained by the same procedure.

The reactor used as the electrolysis cell consisted of a 100 ml. glass beaker with two platinum screen electrodes, each with a surface area of approximately 63 square centimeters, each insulated from the other by a polyethylene screen. The beaker was provided also with a stirring bar and a stopper that contained a tube for nitrogen flush gas. This cell was operated at atmospheric pressure.

The cell as charged with 80 milliliters of electrolyte which was 0.1 molar concentration with respect to tetrapropylammonium tetrafluoroborate and 2.0 molar concentration with respect to methyl 3,5-dimethylbenzoate in acetonitrile as the solvent. Specifically, 2.2 grams of tetrapropylammonium tetrafluoroborate and 26.0 grams of methyl 3,5-dimethyl benzoate were dissolved in acetonitrile to make 80 milliliters of final solution.

The reaction mixture was subjected to electrolysis for about six hours. Current density as 0.008 amperes/square centimeter which was obtained by setting the current flow at 0.5 amperes. The temperature was allowed to fluctuate between 20° to 30°C. The conclusion of the electrolysis was evidenced by a lowering of the rate of formation of the dimer which was determined by gas chromatograpic analysis with the taking of periodic samples. The resulting mixture was removed from the cell, placed in a 300 ml. three-necked round bottom flask equipped with a thermometer, condenser, and electric heating mantle. External heat was applied to the flask by the electric mantle so that the temperature of the mixture reached 33° C. A vacuum of 3 mm Hg. was applied and the acetonitrile removed from the mixture by vacuum distillation at a pot temperature of 30°–35° C. The residue in the flask was ether extracted with three separate extractions of 100 ml of ether. The ether extractions were composited as they contained the desired product, dimethyl 4,4', 6,6'-tetramethylbiphenyl-2,2'-dicarboxylate (DTMBD). The composited ether solution containing the DTMBD was then distilled in a 1000 ml. round bottom flask equipped with an electric heating mantle, a condenser, and a thermometer. The distillation was at atmospheric pressure and 36° C take-off temperature to remove the ether, and then at reduced pressure, 2 mm Hg, and 83°–97° C take-off temperature, approximately 100°–200° C pot temperature, to remove unreacted methyl 3,5-dimethylbenzoate. The residue contained crystalline crude DTMBD. The residue was dissolved in 5 ml. of hot methanol and recrystallized twice by cooling to remove the methanol-soluble impurities and to obtain purified DTMBD product. Yield was 0.3 grams of DTMBD, 98–99% purity.

The procedure given above was repeated except that the current applied was increased to one ampere with a current density of 0.016 amperes/square centimeter. Yield was 0.3 grams of DTMBD, 98–99% purity.

Table I lists data on anodic coupling of methyl 3,5-dimethyl benzoate to prepare dimethyl 4,4' 6,6'-tetramethylbihenyl-2,2'-dicarboxylate. Percent conversion is defined as percent unrecovered starting material. The percent yield is defined as weight of identified product versus weight of unrecovered starting material.

TABLE I

Anodic Coupling Of Methyl 3,5-Dimethyl Benzoate

| Volts | Amperes | Temp. °C | Fara-Days/Mole | Est. Current Eff | Yield | Est. % Conversion |
|---|---|---|---|---|---|---|
| 5.5–5.7 | 0.5 | 25–30 | 0.77 | <10 | 35 | (<40) |
| 6.0–6.5 | 1.0 | 11–28 | 1.4 | <3 | 5 | (60) |

The biphenyl oligomer of methyl 3,5-dimethylbenzoate was hydrolyzed to the diacid using a strong acid for the ester hydrolysis. 0.19 Grams of the ester were stirred in a test tube with 1.06 grams of concentrated sulfuric acid ($H_2SO_4$). The mixture was warmed slowly to approximately 55° C for about 15 minutes until all the ester dissolved. The stirring was continued for an additional 10 to 15 minutes at 50° to 55° C. The reaction mixture was then poured into 5.0 ml of water. The resulting precipitate was filtered and washed repeatedly with small amounts of water (3 to 5 milliliters of water — 5 to 7 times) until all strong acid ($H_2SO_4$) was removed and the pH of the washes was approximately 6. After air drying on sintered glass for one-half hour, the solids were washed twice with chloroform (3 to 5 ml.) to remove most of the remaining unreacted ester. After the solids were dried in a vacuum dessicator, an analysis was made of the 4,4 , 6,6'-tetramethylbiphenyl-2,2'-dicarboxylic acid, TMBDC.

Identification of the purified DTMBD, 98–99% purity, and the dicarboxylic acid derivative, TMBDC, was made by nuclear magnetic resonance (NMR) analysis and by melting point determinations. The NMR readings are reported in parts per million (ppm in terms of the increment ($\delta$) from the standard tetramethylsilane (TMS). The readings are of the chemical shift of the hydrogen located in the following positions, (a) through (e) and are set forth in Table II.

TABLE II

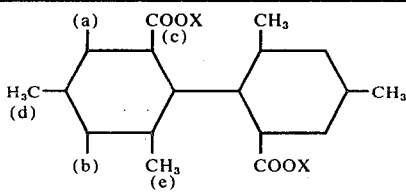

NMR Identification Of DTMBD and TMBDC
Hydrogen Shift From The Standard - In Parts Per Million

| Compound | M.P. | a | b | c | d | e | Solvent |
|---|---|---|---|---|---|---|---|
| (x = CH$_3$) Dimethyl 4,4' 6,6'-tetramethylbiphenyl-2,2'-dicarboxylate (DTMBD) | 153–158 °C | 7.45 | 7.03 | 3.54 | 2.35 | 1.85 | CDCl$_3$ |
| (x = H) 4,4', 6,6'-Tetramethylbiphenyl-2,2'-dicarboxylic acid (TMBDC) | 261–284 (with Decomposition) | 7.56 | 7.23 | —[1] | 2.36 | 1.81 | DMSO(D$_6$) + CDCl$_3$ |

[1]Peak appeared from 8–15% of sample with hydrogen shift of 3.50 indicating presence of DTMBD in 8–15% of the TMBDC.

Note:
Internal standard tetramethylsilane (TMS). All singlet peaks. Areas of peaks are in agreement with proposed formulas within experimental error.

EXAMPLE II

The procedure described in Example I was repeated using methyl 2,4,6-trimethylbenzoate as the starting material. The 2,4,6-trimethylbenzoic acid, 99% pure and having a melting point of 154°–155°C was esterified before electrolysis by refluxing in methanol containing trifluoroacetic anhydride. 47.0 Grams of 2,4,6-trimethylbenzoic acid were dissolved in 200 ml. of trifluoroacetic anhydride at 50°–60° C, cooled to 35° C by immersing the flask in ice water, then 10 grams of purified methanol were added and the mixture stored for ½ hour. The mixture was then poured into 300 ml of 10 (wgt)% of sodium carbonate in water and extracted 3 times with 100 ml each of benzene. The composited benzene was washed once with 50 ml. of the 10 (wgt)% sodium carbonate solution and twice with 100 ml. each of water. The benzene was then dried over calcium sulfate. After filtering, the benzene solution was distilled at atmospheric pressure to remove the benzene. The residue was distilled at a head temperature of 88°–89° C and 2.5 mm Hg. The yield was 34.0 grams of ester.

The reactor used as the electrolysis cell consisted of a 100 ml. glass beaker with two platinum screen electrodes, each with a surface area of approximately 63 square centimeters, each insulated from the other by a polyethylene screen. The beaker was provided with a stirring bar, and a stopper which contained a tube for nitrogen flush gas. This cell was operated at atmospheric pressure.

The cell was charged with 80 milliliters of electrolyte which was 0.1 molar concentration with respect to tetrapropylammonium tetrafluoroborate and 2.1 molar concentration with respect to the methyl 2,4,6-trimethyl benzoate in acetonitrile as the solvent. Specifically, 2.2 grams of tetrapropylammonium tetrafluoroborate and 30.0 grams of methyl 2,4,6-trimethylbenzoate were dissolved in acetonitrile to make 80 milliliters of final solution.

The reaction mixture was subjected to electrolysis for 6 hours. Current density was 0.016 amperes/square centimeter. The temperature was maintained at 20° to 30° C. by external dry ice cooling. The conclusion of the electrolysis was manifested by a lowering of the rate of formation of the dimer determined by gas chromatographic analysis. The resulting mixture was removed from the cell, placed in a 300 ml. three-necked round-bottom flask equipped with a thermometer, condenser, and electric heating mantle. External heat was applied to the flask by the electric mantle so that the temperature of the mixture reached 45° C. A vacuum of 2.5 mm Hg was applied and the acetonitrile removed from the mixture by vacuum distillation. The residue in the flask was ether-extracted with three extractions of 100 ml of ether. The ether extractions were composited as they contained the desired product, dimethyl 2,2', 4,4', 6,6'-hexamethylbiphenyl-3,3'-dicarboxylate (DHMBD). The ether solution containing the DHMBD was then distilled in a 500 ml round bottom flask equipped with an electric heating mantle, a condenser and a thermometer. The solution was distilled at atmospheric pressure and a 61° C. pot temperature to remove the ether and then distilled at reduced pressure, 2.2 mm Hg, and 88°–98° C take-off temperature, 100°–200° C pot temperature, to remove unreacted methyl 2,4,6-trimethyl benzoate. The residue contained crystalline crude DHMBD. The crude DHMBD, approximately 10.2 gms, was distilled at atmospheric pressure, 184° C head temperature and 250° C pot temperature to yield 5.97 grams of solids, 90–95% dimer and approximately 5% trimer based on analyses of gas chromatographs. Purified dimer, M.P. 178°–180°, was obtained by recrystallizing from hot methanol. Table III sets forth the data on anodic coupling of methyl 2,4,6-trimethyl benzoate to obtain DHMBD.

TABLE III

Coupling Of Methyl 2,4,6-Trimethylbenzoate

| Volts | Amperes | Temp. °C | Fara-days/ Mole | Est. Current Eff | Est. % Yield | Conversion |
|---|---|---|---|---|---|---|
| 6.2 | 1.0 | 25–30 | 1.3 | ≳25 | 50 | (67) |

The biphenyl oligomer of methyl 2,4,6-trimethylbenzoate, the DHMBD, was hydrolyzed to the acid using a strong acid for the hydrolysis in the same procedure as described in Example I.

Identification of the purified DHMBD, M.P. 178°–180° C, and the dicarboxylic acid derivative was made by nuclear magnetic resonance (NMR) analysis and melting point determinations, as in Example I. The NMR readings of the chemical shift of the hydrogen located in the following positions (b) through (e) are set forth in Table IV.

TABLE IV

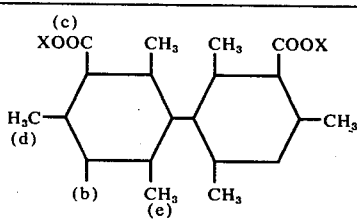

NMR Identification of DHMBD and HMBDC
Hydrogen Shift From The Standard - In Parts Per Million

| Compound | M.P. °C | b | c | d | e | Solvent |
|---|---|---|---|---|---|---|
| (x = CH₃) DHMBD | 178–180 | 7.07 | 3.98 | 2.36 | 1.88 | CDCl₃ |
| (x = H) HMBCD | 285–295 (With Decomposition) | 7.00 | —⁽¹⁾ | 2.32 | 1.82 | DMSO (D₆) + CDCL₃ |

⁽¹⁾Peak appeared from 2–5% of sample with hydrogen shift of 3.95 indicating presence of DHMBD in 2–5% of the HMBDC.
Note:
Internal standard tetramethylsilane (TMS). All singlet peaks. Areas of peaks are in agreement with proposed formulas within experimental error.

I claim:

1. A process for coupling alkyl esters of polyalkylbenzoic acid to prepare polyalkylbiphenylpolycarboxylic acid ester compounds which comprises anodically oxidizing an alkyl ester of a polyakylbenzoic acid in a non-nucleophilic media comprising said ester, a supporting electrolyte and a solvent by applying a source of direct current to said media in liquid phase at atmospheric pressure and temperatures from about −30° to 80° C, wherein the alkyl ester is selected from the group consisting of the alkyl ester of 3,5-dialkylbenzoic acid and the alkyl ester of 2, 4, 6-trialkylbenzoic acid, and each alkyl radical is individually selected from the group of alkyl radicals having 1 to 4 carbon atoms.

2. The process of claim 1 wherein the alkyl radicals of said polyalkylbiphenylpolycarboxylic acid alkyl ester compounds are selected from the group of alkyl radicals consisting of methyl, ethyl and tertiary butyl radicals.

3. The process of claim 2 wherein said polycarboxylic acid ester compound comprises dimethyl 4,4', 6,6'-tetramethylbiphenyl-2,2'-dicarboxylate.

4. The process of claim 2 wherein said polycarboxylic acid ester compound comprises dimethyl 2,2', 4,4', 6,6'-hexamethylbiphenyl-3,3'-dicarboxylate.

5. The process of claim 1 wherein a polyalkylbiphenylpolycarboxylic acid compound is formed which comprises partitioning said polylkylbiphenylpolycarboxylic acid ester compound from said electrolyte and said solvent and hydrolyzing the said ester.

6. The process of claim 5 wherein said acid compound comprises 4,4', 6,6'-tetramethylbiphenyl-2,2'-dicarboxylic acid.

7. The process of claim 5 wherein said acid compound comprises 2,2', 4,4', 6,6'-hexamethylbiphenyl-3,3'-dicarboxylic acid.

8. A polyalkylbiphenylpolycarboxylic acid compound of the structural formula

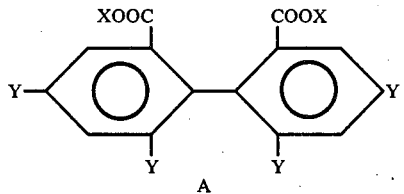

A

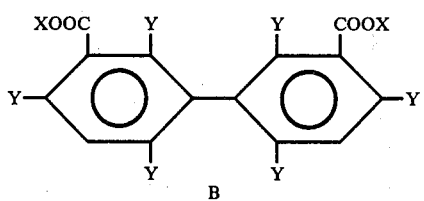

B where X is selected from the group consisting of hydrogen and Y wherein Y is an alkyl radical of from one to four carbon atoms.

9. The compound of claim 8 wherein said compound comprises dimethyl-4,4'-6,6'-tetramethylbiphenyl-2,2'-dicarboxylate.

10. The compound of claim 8 wherein said compound comprises 4,4', 6,6'-tetramethylbiphenyl-2,2'-dicarboxylic acid.

11. The compound of claim 8 wherein said compound comprises dimethyl-2,2', 4,4'-6,6'-hexamethylbiphenyl-3,3'-dicarboxylate.

12. The compound of claim 8 wherein said compound comprises 2,2', 4,4', 6,6'-hexamethylbiphenyl-3,3'-dicarboxylic acid.

* * * * *

UNITED STATES PATENT OFFICE
CERTIFICATE OF CORRECTION

PATENT NO. : 3,992,435
DATED : November 16, 1976
INVENTOR(S) : John A. Donohue, Ellis K. Fields and Harold Hart It is certified that error appears in the above-identified patent and that said Letters Patent are hereby corrected as shown below:

Column 5, line 4, change "EXAMPLE" to read -- EXAMPLE I --.

Column 6, line 58, change "4,4, 6,6'-tetramethylbiphe-" to read -- 4,4', 6,6'-tetramethylbiphe- --.

Column 6, line 64, change "(ppm in terms of" to read -- (ppm) in terms of --.

Column 7, Table II, lines 2-8, change " 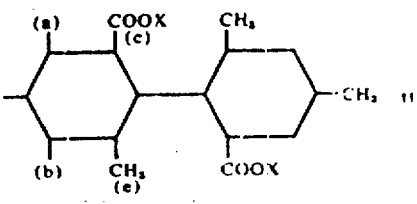 to read -- 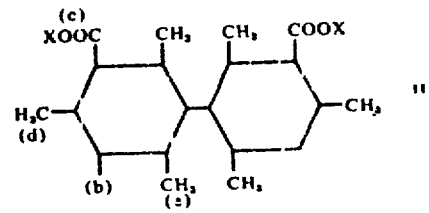 --.

Column 9, Table IV, lines 23-30, change "

UNITED STATES PATENT OFFICE
CERTIFICATE OF CORRECTION

PATENT NO. : 3,992,435
DATED : November 16, 1976
INVENTOR(S) : John A. Donohue, Ellis K. Fields and Harold Hart It is certified that error appears in the above-identified patent and that said Letters Patent are hereby corrected as shown below:

Column 9, line 3, change "Coupling of Methyl 2,4,6-Trimethylbenzoate" to read -- Anodic Coupling of Methyl 2,4,6-Trimethylbenzoate --.

Column 10, line 1, change "polylkylbiphenylpolycar-" to read -- polyalkylbiphenylpolycar- --.

Signed and Sealed this

Eighth Day of March 1977

[SEAL]

Attest:

RUTH C. MASON
Attesting Officer

C. MARSHALL DANN
Commissioner of Patents and Trademarks